US008088395B2

(12) United States Patent
Ghosh (10) Patent No.: US 8,088,395 B2
(45) Date of Patent: Jan. 3, 2012

(54) PHYTOL DERIVED IMMUNOADJUVANTS AND THEIR USE IN VACCINE FORMULATIONS

(75) Inventor: Swapan K. Ghosh, Terre Haute, IN (US)

(73) Assignee: Indiana State University, Terre Haute, IN (US)

( * ) Notice: Subject to any disclaimer, the term of this patent is extended or adjusted under 35 U.S.C. 154(b) by 1582 days.

(21) Appl. No.: 11/295,131

(22) Filed: Dec. 6, 2005

(65) Prior Publication Data

US 2006/0292163 A1      Dec. 28, 2006

Related U.S. Application Data

(63) Continuation of application No. 10/761,571, filed on Jan. 21, 2004, now abandoned.

(51) Int. Cl.
*A61K 45/00* (2006.01)
(52) U.S. Cl. .................. 424/278.1; 424/184.1
(58) Field of Classification Search .............. None
See application file for complete search history.

(56) References Cited

U.S. PATENT DOCUMENTS

| | | | |
|---|---|---|---|
| 4,439,425 A | 3/1984 | Tarcsay et al. | |
| 4,590,190 A | 5/1986 | Saito et al. | |
| 4,605,670 A | 8/1986 | Saito et al. | |
| 4,624,966 A | 11/1986 | Yamamoto et al. | |
| 4,752,612 A | 6/1988 | Saito et al. | |
| 5,102,663 A | 4/1992 | Livingston et al. | |
| 5,122,598 A | 6/1992 | della Valle et al. | |
| 5,280,048 A | 1/1994 | Yamamoto et al. | |
| 5,424,067 A | 6/1995 | Brancq et al. | |
| 5,449,670 A | 9/1995 | Skinner et al. | |
| 5,744,137 A * | 4/1998 | Stone ............... | 424/184.1 |
| 5,961,970 A | 10/1999 | Lowell et al. | |
| 6,063,380 A | 5/2000 | Chedid et al. | |
| 6,231,859 B1 | 5/2001 | Kensil | |
| 6,248,329 B1 * | 6/2001 | Chandrashekar et al. | 424/191.1 |
| 6,258,796 B1 | 7/2001 | Richards | |
| 6,261,573 B1 | 7/2001 | Loebelenz et al. | |
| 6,262,029 B1 | 7/2001 | Press et al. | |
| 6,288,128 B1 | 9/2001 | Yamamoto et al. | |
| 6,299,884 B1 | 10/2001 | Van Nest et al. | |
| 6,451,325 B1 | 9/2002 | Van Nest et al. | |
| 6,458,373 B1 | 10/2002 | Lambert et al. | |
| 6,525,035 B1 | 2/2003 | Danilov et al. | |
| 2002/0082298 A1 | 6/2002 | Fluehmann et al. | |

FOREIGN PATENT DOCUMENTS

| | | |
|---|---|---|
| WO | 97/22333 | * 6/1997 |
| WO | WO 02/083058 | 10/2002 |
| WO | WO 02/083122 | 10/2002 |
| WO | WO 03/013420 | 2/2003 |

OTHER PUBLICATIONS

Arnhold et al, Toxicol. Sci. 66:274-282, 2002.*
The Dictionary of Immunology, Herbert et al eds, Academic Press, 1995 definition of vaccine, pp. 1-3.*
Ellis, R.W. (Chapter 29 of "VACCINES" [Plotkin, S.A. et al. (eds) published by W. B. Saunders company (Philadelphia) in 1988.*
Feng et al (Infection and Immunity, 64(1):363-365, 1996).*
Lycke et al, Essen. Mucosal. Immunol., 1996, pp. 563-580.*
Pokric (Periodicum Biologorum, 101(4):283-302, 1999).*
(Macy, Seminars in Veterinary Medicine and Surgery, 12(3):206-211, 1997).*
Lim et al (FASEB Journal 19 (4, Suppl. S, Part 1): pA897-A898, Mar. 4, 2005.*
Gupta, Rajesh K. et al., *Adjuvants—a balance between toxicity and adjuvanticity*, Vaccine, vol. 11, Issue 3, 1993, pp. 293-306.
O'Hagan, Derek T. et al., *Recent advances in vaccine adjuvants: the development of MF59 emulsion and polymeric microparticles*, Molecular Medicine Today, Feb. 1997, pp. 69-75.
Sing, Manmohan et al., *Advances in vaccine adjuvants*, Nature Biotechnology, Nov. 1999, vol. 17, pp. 1075-1081.
Neurath, A. Robert et al., *Anti-HIV-I activity of cellulose acetate phthalate: Synergy with soluble CD4 and induction of "dead-end" gp41 six-helix bundles*, BMD Infectious Diseases Apr. 30, 2002.
Cribbs, David H. et al., *Adjuvant-dependent modulation of $T_h1$ and $T_h2$ responses to immunization with β-amyloid*, International Immunology, 2003, vol. 15, No. 4, pp. 505-514.
Phytol-based novel adjuvants in vaccine formulation: 1. assessment of safety and efficacy during stimulation of humoral and cell-mediated immune responses—So-Yon Lim, Matt Meyer, Richard A. Kjonaas and Swapan K. Ghosh. Journal of Immune Based Therapies and Vaccines 2006; Oct. 30, 2006.
Phytol-based novel adjuvants in vaccine formulation: 2. assessment of efficacy in the induction of protective immune responses to lethal bacterial infections in mice. So-Yon Lim, Adam Bauermeister, Richard A. Kjonaas and Swapan K. Ghosh. Journal of Immune Based Therapies and Vaccines 2006; Oct. 23, 2006.

* cited by examiner

*Primary Examiner* — Patricia A Duffy
(74) *Attorney, Agent, or Firm* — Barnes & Thornburg LLP (57) ABSTRACT

This invention relates to a novel immunoadjuvant, an adjuvant component, and vaccines containing the adjuvant component. The adjuvant includes phytol or a phytol derivative. The adjuvant component, when combined with a soluble or particulate antigen, provides a vaccine with an enhanced ability to induce both humoral and cytotoxic immune responses while displaying reduced toxicity and/or adverse side effects over vaccines that include the antigen but without the benefit of this adjuvant component.

20 Claims, 7 Drawing Sheets

PHYTOL DERIVED IMMUNOADJUVANTS AND THEIR USE IN VACCINE FORMULATIONS

CROSS-REFERENCE TO RELATED APPLICATIONS

This application is a continuation and claims priority from U.S. patent application Ser. No. 10/761,571, filed Jan. 21, 2004 now abandoned, which is incorporated herein by reference in its entirety.

BACKGROUND

The present invention relates to immunoadjuvants that include phytol or a phytol derivative and the use of the immunoadjuvants in a pharmaceutical formulation to effect treatment by augmenting immunogenicity and effectiveness of vaccines.

Vaccines are used to provide effective immunity to prevent infection and even cancer. With the introduction of widespread immunization in the last century, diseases such as diphtheria, tetanus, polio, small pox, and pertussis have been significantly reduced if not eliminated. Moreover, new generations of vaccines are constantly being sought after for treatment of diseases such as AIDS, hepatitis, and herpes.

Vaccines are meant to stimulate the individual's specific and non-specific immune responses. Vaccines are accompanied by an adjuvant which can increase the efficacy of the vaccine by a variety of actions, including retaining the vaccine in the body or at the site of injection for a significantly long period of time, eliminating or reducing degradation and/or excretion, and recruiting or directing macrophages and other antigen-presenting cells (APCs) to augment humoral and/or cellular immune responses to the pathogen or associated antigens. However, many adjuvants, while effective, are also often toxic to humans. These adjuvants can cause severe adverse inflammatory reactions. Therefore, while adjuvants can be effective in enhancing the immunogenicity of the antigens in the vaccines, they can also induce severe side reactions.

The only adjuvant currently accepted by the FDA for use in humans is aluminum hydroxide or alum. While this adjuvant presents fewer instances of adverse reactions, it is not as effective in inducing humoral or cellular immune responses as other adjuvants, such as incomplete Freund's adjuvant (IFA) or complete Freund's adjuvant (CFA, which is IFA plus mycobacterial components). Both Freund's adjuvants, for example, are used in animals (other than humans) to produce antibodies for treatment and diagnosis under strict regulations of USDA and Public Health Service (PHS). While CFA/IFA are not approved for use in humans because they can be quite toxic to certain individuals, they are still considered as the gold standard in adjuvant formulation. In countries other than the United States, IFA is used in many vaccine formulations.

A safer, non-toxic, non-carcinogenic adjuvant which elicits an enhanced immune response for the antigens in the vaccine formulation would be of immense value to both human and animal welfare. The present invention addresses the above described problems and provides a variety of benefits and advantages.

SUMMARY OF THE INVENTION

The present invention relates to immunoadjuvants that include phytol, isophytol, or a phytol derivative and the use of the immunoadjuvants to elicit an immune response. Various aspects of the invention are novel, nonobvious, and provide various advantages. While the actual nature of the invention covered herein can only be determined with reference to the claims appended hereto, certain forms and features, which are characteristic of the preferred embodiments disclosed herein, are described briefly as follows.

In one form, the present invention provides a composition that includes a vaccine preparation in unit dosage form comprising: an effective amount of an antigen; an adjuvant component comprising phytol, isophytol, or a phytol derivative; and optionally a carrier.

In another form, the present invention provides a method of enhancing the immunogenicity of a vaccine composition. The method comprises selecting an antigen that induces a desired immunogenic response in a mammal; combining the antigen with phytol, isophytol, or a phytol derivative in a physiologically acceptable carrier; and treating a mammal with the vaccine composition in an amount effective to induce the immunogenic response. In preferred embodiments, the vaccine formulation includes the antigen in a lower effective dose than another vaccine formulation that includes the same antigen but without the benefit of or in the absence of the phytol or a phytol derivative. The preferred vaccine formulation still elicits the desired immunogenic response substantially the same as the vaccine that does not include the phytol, isophytol, or phytol derivative.

In another form, the present invention provides a method for inducing full spectra of immune responses, namely antibody, NKT cells, and helper-cytotoxic effector T lymphocytes to soluble and insoluble antigens. The method comprises selecting an antigen that induces a desired immunogenic response in a mammal; combining the antigen with phytol, isophytol, or a phytol derivative in a physiologically acceptable carrier; and treating a mammal with the vaccine composition in an amount effective to induce the immunogenic response.

In still yet another form, the present invention provides a method of treating a patient in need thereof with a vaccine. The method comprises administering to the patient a vaccine composition comprising an antigen and an adjuvant component including phytol, isophytol, or a phytol derivative in a physiologically acceptable carrier.

Further objects, features, aspects, forms, advantages and benefits shall become apparent from the description and drawings contained herein.

BRIEF DESCRIPTION OF THE DRAWINGS

FIGS. 3A-3F are scanned images of spleens obtained from BALB/c mice treated
with adjuvants: A, (PBS); B, pristane; C, Incomplete Freund's adjuvant (IFA); D, phytol; E, Complete Freund's adjuvant (CFA); and F, reduced phytol (phytanol).

DETAILED DESCRIPTION OF THE INVENTION

For the purposes of promoting an understanding of the principles of the invention, reference will now be made to the embodiments illustrated herein and specific language will be used to describe the same. It will nevertheless be understood that no limitation of the scope of the invention is thereby intended. Any alterations and further modifications in the described formulations, compositions, and/or treatments, and any further applications of the principles of the invention as described herein, are contemplated as would normally occur to one skilled in the art to which the invention relates.

The present invention provides a novel immunoadjuvant or an immunoadjuvant component for use in a pharmaceutical or vaccine formulation. The adjuvant component can include phytol or a phytol derivative. The vaccine formulation can include, in addition to the adjuvant or adjuvant component, one or more soluble or membranous antigens, and optionally one or more of a carrier unlinked, or covalently or hydrophobically linked, an emulsifier, and a surface active agent. The vaccine formulation and immunoadjuvant prepared according to the present invention can be used to treat mammals including humans either phrophylactically or therapeutically as desired or deemed medically expedient.

The adjuvant component for use in the present invention can include phytol, isophytol, phytanol, and/or a phytol derivative. Phytol is a commercially available compound that is derived from vitamin E ($\alpha$-tocopherol) or from chlorophyll as well as other naturally occurring species. Phytol can be considered a fatty alcohol or, more specifically, a branched chain fatty alcohol and includes an unsaturated beta hydroxy group. (See FIGS. 1A and 1B for phytol and isophytol, respectively.)

Figure 1:
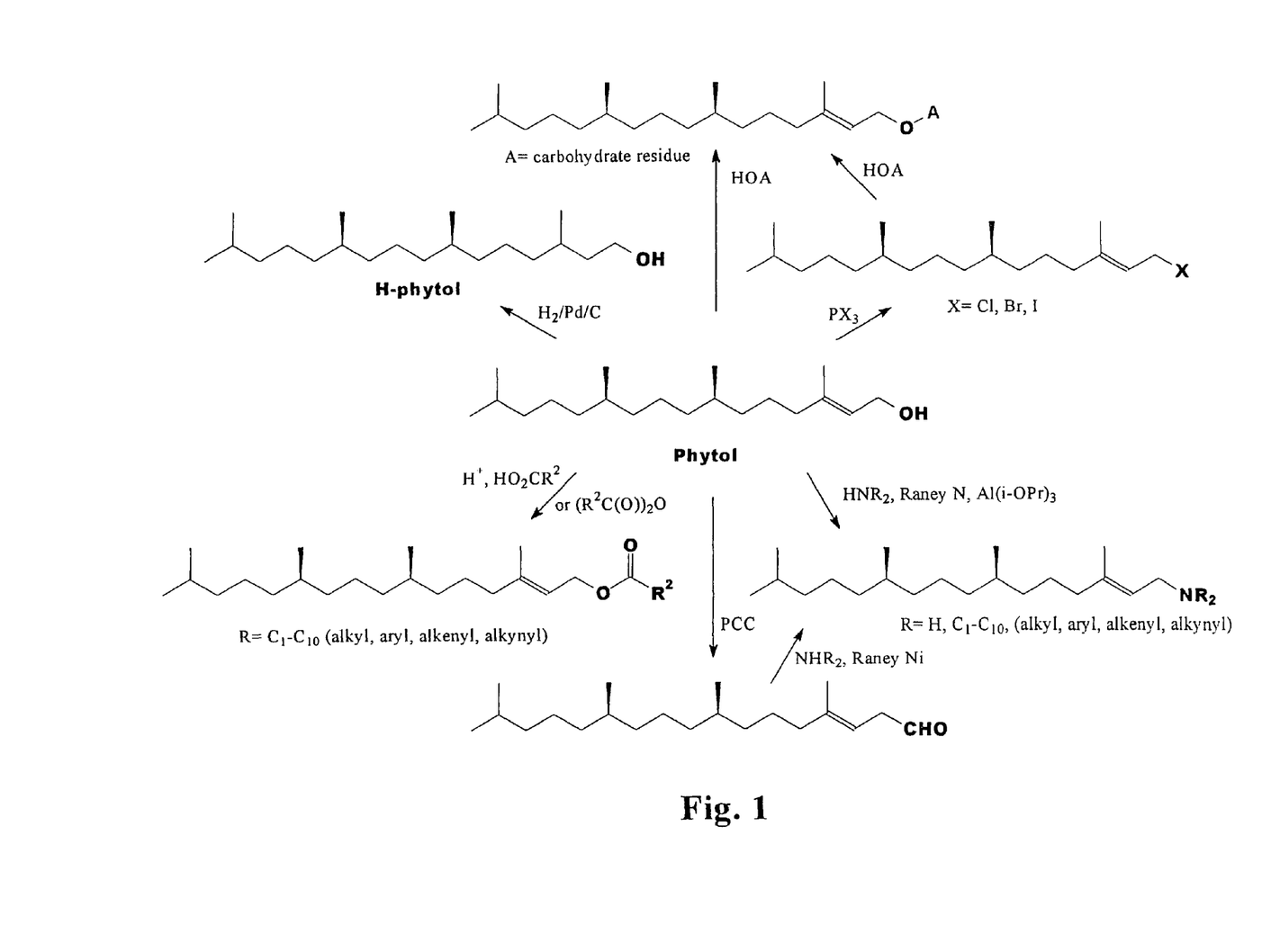
FIG. 1 is a scheme illustrating various synthetic strategies for synthesizing phytol derivatives.
Figure 1A:
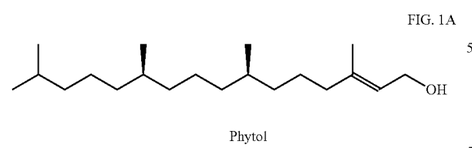

FIG. 1A

Phytol

Figure 1B:
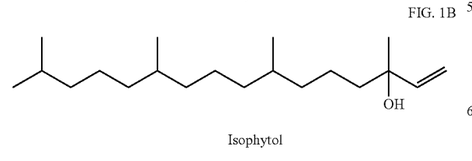

FIG. 1B

Isophytol

Figure 2:
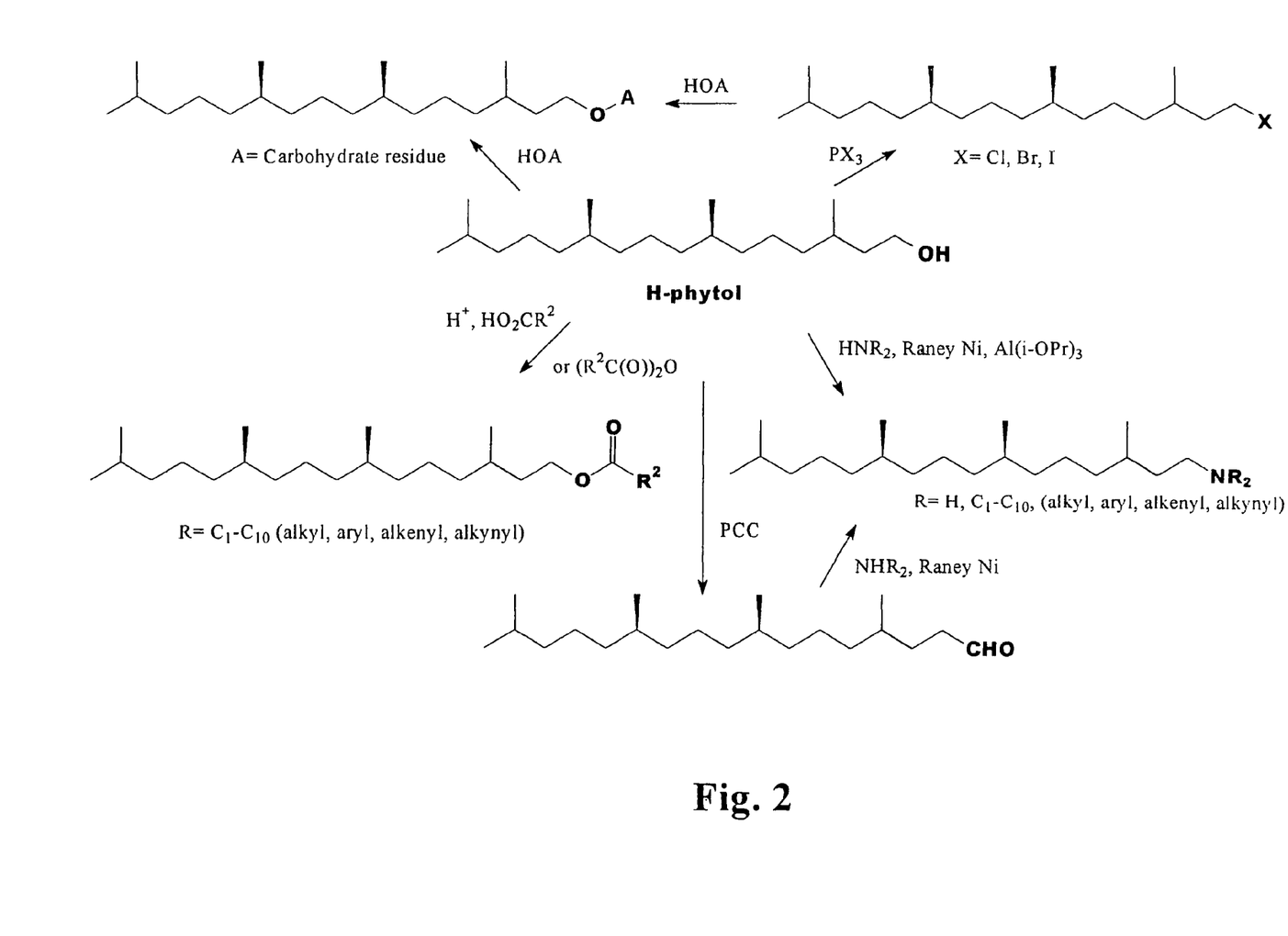
FIG. 2 is a scheme illustrating various synthetic strategies for synthesizing reduced phytol or phytanol (H-phytol) derivatives.
Figure 3A:
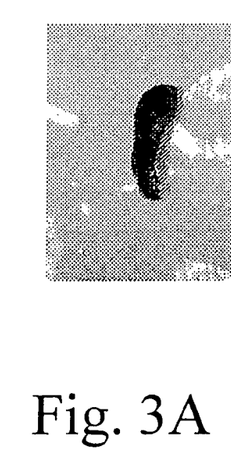
Figure 3B:
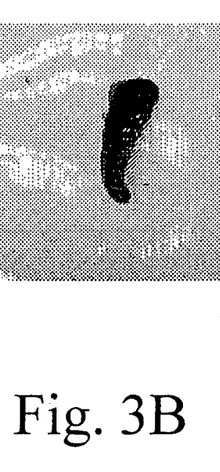
Figure 3C:
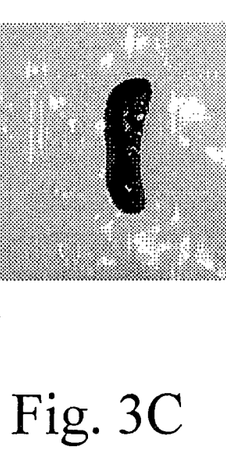
Figure 3D:
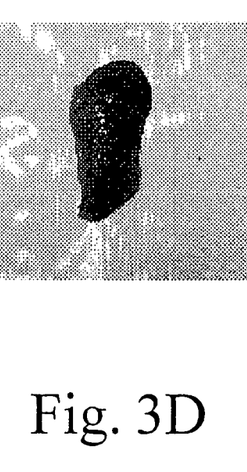
Figure 3F:
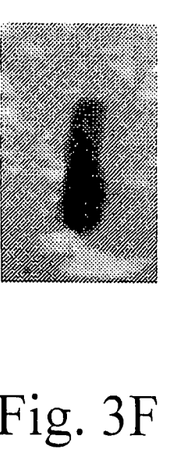

Phytol derivatives as described herein include reduced phytol (or H-phytol/phytanol) and reduced isophytol in which the unsaturated group in each species has been reduced with hydrogen. Reduced phytol or H-phytol will hereafter be referred to as phytanol, unless otherwise stated. The double bond in phytol (or isophytol) can be reduced using palladized carbon and hydrogen gas under standard conditions. FIG. 1 provides a synthetic scheme for the preparation of representative examples of various phytol derivatives that are included within the scope of the present invention. FIG. 2 provides a similar scheme for the preparation of various examples of reduced phytol derivatives that are included within the scope of the present invention. Similar synthetic strategies are envisioned to prepare isophytol derivatives. Examples of the phytol derivatives include halogenated phytol, halogenated phytanol, an aminated phytol or phytanol, and phytol or phytanol derivatives in which the hydroxy group has been substituted with a nitro group, aldehyde group, or esterified phytol or phytanol, in which hydroxyl group has been used to esterify a carboxylic acid to form an ester. Other phytol derivatives can be carried out using standard procedures of organic chemistry. It will be understood that either phytol, isophytol or reduced phytol, reduced isophytol can be used in the following examples. Examples of the various transformations include oxidation of the hydroxyl group using pyridine chlorochromate (PCC) or activated $MnO_2$. Amine phytol derivatives can be prepared with phytol aldehydes (from PCC reaction) using a suitable primary or secondary amine and Raney Ni catalyst. The amine derivatives can be used to prepare antigen-phytol conjugates; for example, phytolated lysine or polylysine can be used directly or as a conjugate with different antigens with lysine serving as a linker. Halogenated phytol derivatives can be prepared by substituting the hydroxyl group with chlorine using $PCl_3$ in DMF (or $PCl_5$) or bromine using $PBr_3$ in pyridine or with iodine using iodine or sodium iodide and a Lewis base, such as, boron trifluoride etherate ($BF_3.OEt_2$), triphenyl phosphine, or phosphorous metal. The halogenated phytol derivatives also can be used to react with carbohydrates to prepare a phytol-carbohydrate (or phytanol-carbohydrate) complex. Examples of preferred carbohydrates that can be coupled with phytol (or phytanol) include: monoschharides, oligosachharides, polysachharides, mannitol, sorbitol, glycosaminoglycans, chondrosine, and arabans. Various phytol derivatives can be prepared according to established procedures, for example, suitable synthetic conditions for preparing the phytol derivatives can be ascertained from Richard Larock, "Comprehensive Organic Transformations", VCH Publishers, Inc., 1989, and references cited therein.

Representative examples of phytol derivatives for use in the present invention include: hydrogenated phytol (3,7,11,15-tetramethyl-1-hexadecanol); chlorinated phytol (1-chloro-3,7,11,15-tetramethyl hexadec-2-ene); iodinated phytol (iodo-3,7,11,15-tetramethyl hexadeca-2-ene); aminated phytol (1-amino-3,7,11,15-tetramethyl hexadec-2-ene); 3,7,11,15-tetramethyl-hexadec-2-en-1-al; 3,7,11,15-tetramethyl-1-hexadecanal; 3,7,11,15-tetramethyl-1-hexadec-2-enyl acetate; 3,7,11,15-tetramethyl-1-hexadecanyl acetate; 1-chloro-3,7,11,15-tetramethyl hexadecane; 1-iodo-3,7,11,15-tetramethyl hexadecane; 1-amino-3,7,11,15-tetramethyl hexadecane; 1-methyl amino-3,7,11,15-tetramethyl hexadecane and stereoisomers, and mixtures thereof.

The immunoadjuvant component can contain phytol or the phytol derivative in amounts from between about 100 wt % and about 20 wt %. Other species in the immunoadjuvant component can include other adjuvants such as aluminum hydroxide, IFA, vegetable oil, and the like.

The adjuvant component can be combined with a wide variety of antigens to provide the vaccine formulation. For example, the vaccine formulation can include antigens specific for a variety of pathogens or diseases including viruses, bacterial, fungal, protozoan antigens, and/or tumor associated antigens. The antigen can include T-lymphocyte-dependent proteins, haptenated proteins, haptenated peptides, peptides, and the like as well as or T-independent polysaccharides and haptens conjugated to polysaccharides. The antigen can be polysaccharides, toxins, and toxoids derived from pathogens. Examples of various antigens for use with the present invention include antigens derived from or including either whole or in part, viruses, such as, but not restricted to: feline leukemia virus (FeLV), feline immunodeficiency virus (FeIV), bovine LV, HIV-1, HIV-2, HTLV-1, HTLV-II, rabies, measles, hepatitis B, hepatitis C, hoof and mouth disease, influenza viruses, parainfluenza viruses, mumps virus, adenoviruses, respiratory syncytial virus, Epstein-Barr virus, rhinoviruses, polioviruses, coxsackieviruses, echoviruses, rubeola virus, rubella virus, varicell-zoster virus, herpes viruses (human and animal), herpes simplex virus, parvoviruses (human and animal), cytomegalovirus, hepatitis viruses, human papillomavirus, alphaviruses, flaviviruses, bunyaviruses, rabies virus, arenaviruses, filoviruses, canine distemper virus, canine contagious hepatitis virus, feline calicivirus, feline rhinotracheitis virus, TGE virus (swine), cholera viruses, and tetanus viruses.

Examples of bacterial antigens that can be used with the present invention include, but are not restricted to, antigens derived from or which include either whole or in part: anthrax, diphtheria, Lyme disease, or tuberculosis; or protozoans, such as *Babeosis bovis* or *Plasmodium, Helicobacter pylori, Chlamydia pneumoniae, Chlamydia trachomatis, Ureaplasma urealyticum, Mycoplasma pneumoniae, Staphylococcus* spp., *Staphylococcus aureus, Streptococcus* spp., *Streptococcus pyogenes, Streptococcus pneumoniae, Streptococcus viridans, Enterococcus faecalis, Neisseria meningitidis, Neisseria gonorrhoeae, Bacillus anthracis, Salmonella* spp., *Salmonella typhi, Vibrio chlorea, Pasteurella pestis, Pseudomonas aeruginosa, Campylobacter* spp., *Campylobacter jejuni, Clostridium* spp., *Clostridium difficile, Mycobacterium* spp., *Mycobacterium tuberculosis, Treponema* spp., *Borrelia* spp., *Borrelia burgdorferi, Leptospria* spp., *Hemophilus ducreyi, Corynebacterium diphtheria, Bordetella pertussis, Bordetella parapertussis, Bordetella bronchiseptica, hemophilus influenza, Escherichia coli, Shigella* spp., *Erlichhia* spp., and *Rickettsia* spp. to name just a few examples.

Examples of fungal antigens that can be used with the present invention include, but are not restricted to, antigens derived from or which include either whole or in part: *Aspergillus fumigatus, Candida albicans, Histoplasma capsulatum, Coccidioides immiti,* or *Blastomyces dermatiditis,* to name just a few examples.

Tumor associated antigens can be native, recombinant, or synthetic immunogenic polypeptides or peptide fragments. Such tumor associated antigens include, but are not limited to, killed tumor cells and lysates thereof, MAGE-1 or MAGE-3 and peptide fragments thereof, human chorionic gonadotropin (HCG) and peptide fragments thereof, carcinoembryonic antigen (CEA) and peptide fragments thereof, alpha fetoprotein (AFP) and peptide fragments thereof, pancreatic oncofetal antigen and peptide fragments thereof, MUC-1 and peptide fragments thereof, CA 125, 15-3, 19-9, 549, 195 and peptide fragments thereof, prostate-specific antigens (PSA) and peptide fragments thereof, prostate-specific membrane antigen (PSMA) and peptide fragments thereof, squamous cell carcinoma antigen (SCCA) and peptide fragments thereof, ovarian cancer antigen (OCA) and peptide fragments thereof, pancreas cancer associated antigen (PaA) and peptide fragments thereof, Her1/neu and peptide fragments thereof, gp-100 and peptide fragments thereof, mutant K-ras proteins and peptide fragments thereof, mutant p53 and peptide fragments thereof, truncated epidermal growth factor receptor (EGFR), and chimeric protein $p210^{BCR-ABL}$.

The vaccine formulation can include the immunoadjuvant component and antigen in an effective immunoadjuvant:antigen ratio to elicit an immunogenic response. Preferable the immunoadjuvant:antigen ratio in the present invention ranges between about 20:80 wt % (wt:wt, adjuvant component:antigen component) to about 50:50 wt %. More preferably, the vaccine formulation can include the adjuvant component and the antigen component in a weight ratio ranging between about 10:30 wt % to about 10:20 wt %. The upper limit of phytol in the vaccine formulation can be selected to be about 40 mg (50 µl) and for phytanol about 80-100 mg (100-125 µl).

The vaccine formulation can include a carrier such as water, preferably in buffered saline, or an oil-and-water emulsion, or other physiologically suitable medium. The vaccine formulation can include optional components in addition to the carrier. The optional components can include surfactants, emulsifiers, liposomes, cyclodextrin, and the like.

One of the other optional components can include an emulsifying agent. Examples of emulsifying agents that can be included in the present invention include naturally derived materials such as gums from trees, vegetable protein, sugar-based polymers such as alginates and cellulose specific examples including: sorbital, mannitol, saccharose, glucose, and the like; oxypolymers or polymers having a hydroxide or other hydrophilic substituent on the carbon backbone having surfactant activity, for example, povidone, polyethylene glycol, polyvinyl alcohol, and glycol ether-based mono- and poly-functional compounds; long chain fatty-acid-derived compounds such as ethers of fatty acids, esters of fatty acids, glycerol, polyol lecithins, fatty acids, or alcohols condensed with ethylene and/or propylene oxide. Liquid emulsifiers are preferred.

The emulsifying agent can be included in the vaccine formulation in a desired amount selected to provide an emission stable for treatment of animals including humans. Preferably the emulsifier is included in an amount selected to maintain a stable, uniform, or homogeneous emulsion. In selected embodiments, the selected amount can be between about 0.18 wt % and about 0.5 wt % based upon the total weight of the vaccine formulation.

When the vaccine formulation includes a surfactant, the surfactant can be included in an amount ranging between about 0.15 ml and 0.40 ml. Examples of surfactants include, but are not restricted to, mannide monooleates, 1,4-sorbitan mono- and triesters, polysorbate 80, polyoxyethylene derivatives of stearic acid (sold under the trade name MYRJS®). The adjuvant component can be selected to provide enhanced properties for the vaccine formulation. Such enhanced properties can include reduced toxicity, increased immunogenicity for the antigen, and longer retention at the site of injection and/or within the body in general. Consequently, a vaccine formulation can be prepared that includes the antigen and the adjuvant component of the present invention. This vaccine formulation can include the antigen in amounts lower than that amount, which can be provided with the vaccine alone or with the vaccine in combination with another antigen such as aluminum hydroxide and still provide an equal or enhanced immunogenic response. In preferred embodiments, the vaccine formulation of the present invention can be formulated to include the antigen in amounts ranging from about 10% to about 30% less than that found in similar vaccine formulations formulated without the phytol or phytol derivative as described herein. In selected embodiments, the antigen can be included in the formulations of the present invention in amounts between about 5-100 μg.

As noted above the vaccine formulation of the present invention can include the antigen directly bonded to the phytol, phytanol or other phytol derivative (referred to below as "the antigen phytol conjugate"). For example, the phytanol or other phytol derivative can be directed bonded to a protein or a carbohydrate. The vaccine formulation of this embodiment can include the antigen-phytol conjugate in amounts effective to induce an immunological response. More preferably the vaccine formulation in unit dosage form can include the antigen-phytol conjugate in an amount between about 4 to about 100 micrograms.

The formulation that includes the antigen-phytol conjugate can be used in combination with a surfactant. Preferably the surfactant and the antigen-phytol conjugate are combined in equal volume amounts, optionally with a carrier or buffer solution. Preferably a liquid vaccine formulation with a carrier includes the surfactant in an amount between about 0.05 and about 0.1% (wt/v: surfactant/carrier).

The adjuvant component of the present invention can be prepared by combining the phytol or the phytol derivative in a suitable medium for the vaccine. If the medium is physiological saline, an emulsifier can be added to provide a homogeneous mixture or suspension. Additional components can be added as desired. The additional components can include an emulsifier, surface active agent, phospholipids, and the like.

Non limiting examples of commercially available emulsifiers and/or surfactants for use in the present invention include various molecular weights of poly(ethylene glycol) (PEG 300, PEG 400, PEG 600, and PEG 800), sorbitan derivatives, and/or sorbitan esters of fatty acids such as sorbitan monolaurate, sorbitan monopalmitate sorbitan monostearate, sorbitan tristearate and sorbitan trioleate and mixtures of these compounds Commercially available emulsifiers useful in the present invention are sold under the trade names TWEEN®, ARLACEL®, and SPAN®, (available from ICI America's, Inc., Wilmington, Del.).

The vaccine formulation according to the present invention can be prepared by combining either the phytol, or the phytol derivative and one or more antigens in a suitable carrier. The order of addition is not critical to the practice of the present invention. Alternatively, a liquid adjuvant component such as that described above can be combined or admixed with a suitable antigen, which may or may not be dissolved or suspended in a liquid medium. Additional components such as surfactants, stabilizers, and alum can also be combined with the antigen and adjuvant component. Again, the order of addition is not critical to the practice of the present invention. After the antigen and adjuvant or adjuvant component and any additional components have been combined, the resulting mixture is thoroughly stirred to ensure that the resulting formulation is homogeneous.

The vaccine formulation can be administered by any medically acceptable route including oral, nasal, mucosal, or injected (preferably intramuscular injection).

For the purposes of promoting further understanding and appreciation of the present invention and its advantages, the following Examples are provided. It will be understood, however, that these Examples are illustrative and not limiting in any fashion.

Example 1

Preparation of 2,3-Dihydrophytol (Phytanol or H-Phytol)

To a solution of 1.00 g phytol in dry tetrahydrofuran was added 0.10 g 5% palladium on carbon. The mixture was allowed to stir 24 h under hydrogen at 1 atm. The catalyst was removed by centrifugation and the solvent was then removed by rotary evaporation. The resulting oil was purified by molecular distillation at about 100° C. and 0.1 mm Hg to give a colorless oil: $^1$H NMRδ (ppm) 0.90 (d, ~15H), 1-1.8 (m, ~25H), 3.7 (t, 2H).

Hydrogenation of phytol can also be accomplished using Raney nickel and hydrogen to yield phytanol as referenced in Bendavid, A., Burns, C. J., Leslie, D. F., Hashimoto, K., Ridley, D. D., Sandanayake, S., and Wieczorek L., *J. Org. Chem.* (2001), 66, 3709-3716; Kim, T., Chan, K. C, and Crooks, R. M., *J. Am. Chem. Soc.* (1997) 119, 189; and Jellum, E., Eldjarn, L., and Try, K., *Acta Chem. Scand.* (1966), 20, 2335.

Example 2

Preparation of Halogenated Phytol/Phytanol

Hologenated phytol can be prepared according the procedure outlined below. The procedure shown below is a general one and can be found in the above references, and in particular in Bendavid, A., Burns, C. J., Leslie, D. F., Hashimoto, K., Ridley, D. D., Sandanayake, S., and Wieczorek, L., *J. Org. Chem.* (2001), 66, 3709-3716.

Example 3

Preparation of Phytanyl Glucose/Phytanyl Mannose

Phytanyl glucose has been previously reported. (1, 2). The procedure used by Hato and coworkers (2) to make this compound in moderate yield is the same procedure that they used to make some similar acetals several years earlier (3). However, recent reports (4, 5, 6) of the preparation of some similar lipidated carbohydrate acetals appear to offer even better ways of making phytanyl glucose. Hinguchi and coworkers (4) converted glucose acetate to a bromide by treating with HBr and then converted this to an acetal by treating it with a long-chain alcohol, $AgClO_4$ and $AgCO_3$. It is envisioned that a procedure, as shown below, can be used with phytanol.

Alternatively, a phytanyl glucose conjugate can be prepared by adapting a procedure reported by Clausen and coworkers (glucose acetate, ROH, $BF_3 \cdot OEt_2$, $CH_2Cl_2$) (5) or by the procedure disclosed by Konstantinovic and coworkers (glucose acetate, ROH, $SnCl_4$) (6). A similar scheme can be adopted to make phytanylated manose.

(1) Masakatsu, H.; Hiroyuki, N. Japanese patent number JP2002226597
(2) Hato, M.; Minamikawa, H.; Salkar, R. A.; Matsutani, S. *Langmuir*, 2002, 18, 3425-3429.
(3) Minamikawa, H.; Murakami, T.; Hato, M. *Chem. Phys. Lipids*, 1994, 72, 111-118.
(4) Higuchi, R.; Mori, T.; Sugata, T.; Yamada, K.; Miyamoto, T. *European Journal of Organic Chemistry*, 1999, 3175-3178.
(5) Clausen, M. H.; Jorgensen, M. R.; Thorsen, J.; Madsen, R. *J. Chem. Soc., Perkin Trans.* 1, 2001, 543-551.
(6) Konstantinovic, S.; Predojevic, J.; Gojkovic, S.; Pavlovic, V. *Indian Journal of Chemistry*, 2003, 42B, 666-669.

Example 4

Comparison of Phytol and Phytol Derivatives with Various Commercially Available Adjuvants Phytol-Induced Changes in BALB/c Mice The efficacy and side effects (such as toxicity, carcinogenic properties, and autoimmunogenic properties) of phytol and reduced phytol or phytanol (H-phytol) as adjuvants were compared with those of other known adjuvants that serve as the gold standard. Groups of 8-12 week old and gender matched BALB/c mice (n=21) were injected intraperitoneally with phytol (25-50 μl=20-40 mg/ml injected vaccine formulation) to determine toxicity. Similar studies were done with reduced phytol (phytanol) using 11 BALB/c mice. LD50 for phytol is 40 mg/ml and for phytanol >40 mg/ml. For comparison, equivalent concentrations/volumes of other Freund's adjuvants, a mineral oil pristane and a control (phosphate buffered saline) were tested for toxicity in terms of splenomegaly and local granuloma. The results shown in FIGS. 3A-3F show comparable splenomegaly with phytol and CFA, but none with phytanol. Phytol is milder than CFA in terms of splenomegaly and granuloma. Phytanol (reduced phytol) shows no granuloma.

Carcinogenic Potential Assessment

Figure 4:
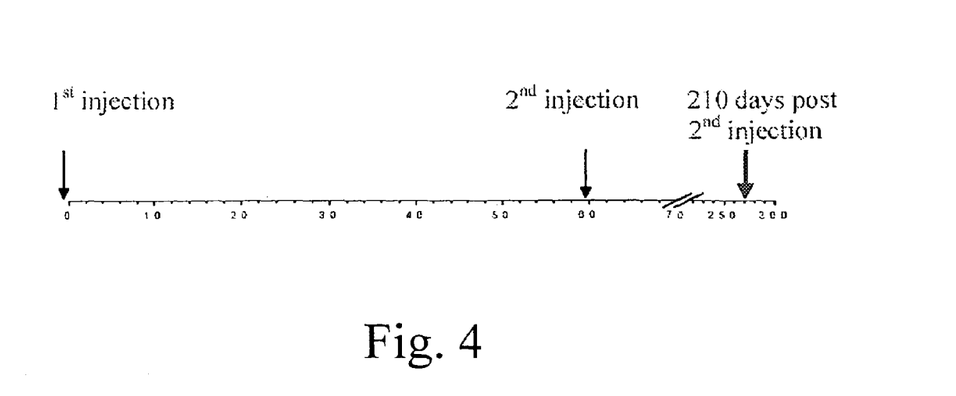
FIG. 4 is a time line illustrating the treatment regime used to evaluate the peritoneal plasmoacytomagenesis in BALB/c mice treated with pristane, phytol, or phytanol.
Figure 4A:
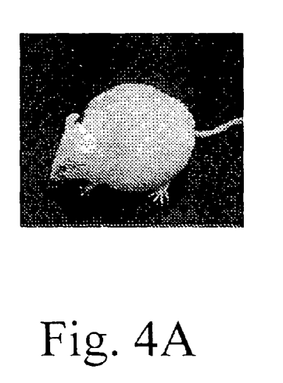
FIGS. 4A-4C are scanned images of mice injected with the following: A, pristane; B, phytol; and C, phytanol; indicating that plasmacytoma was not observed in the mice treated with phytol or phytanol.
Figure 4B:
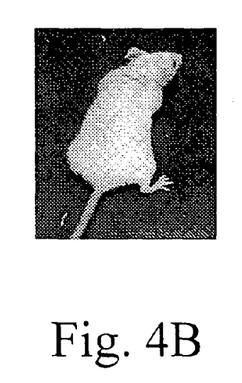
Figure 4C:
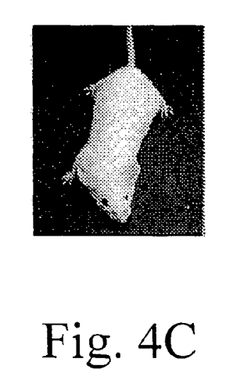

Groups of BALB/c mice were treated with two intraperitoneal injections (0.5 ml of pristane, and 50 μl of phytol and Phytanol each, 2 months apart). After 210 days, BALB/c mice injected with only pristane showed appearance of ascites containing plasmacytoma cells. The results in FIG. 4 clearly show that neither phytol nor phytanol (reduced phytol) induces plasmacytoma, but it was observed that pristane, a mineral oil component of many adjuvants, does induce plasmacytomado.

Autoimmune Reactivity Assessment

Figure 5:
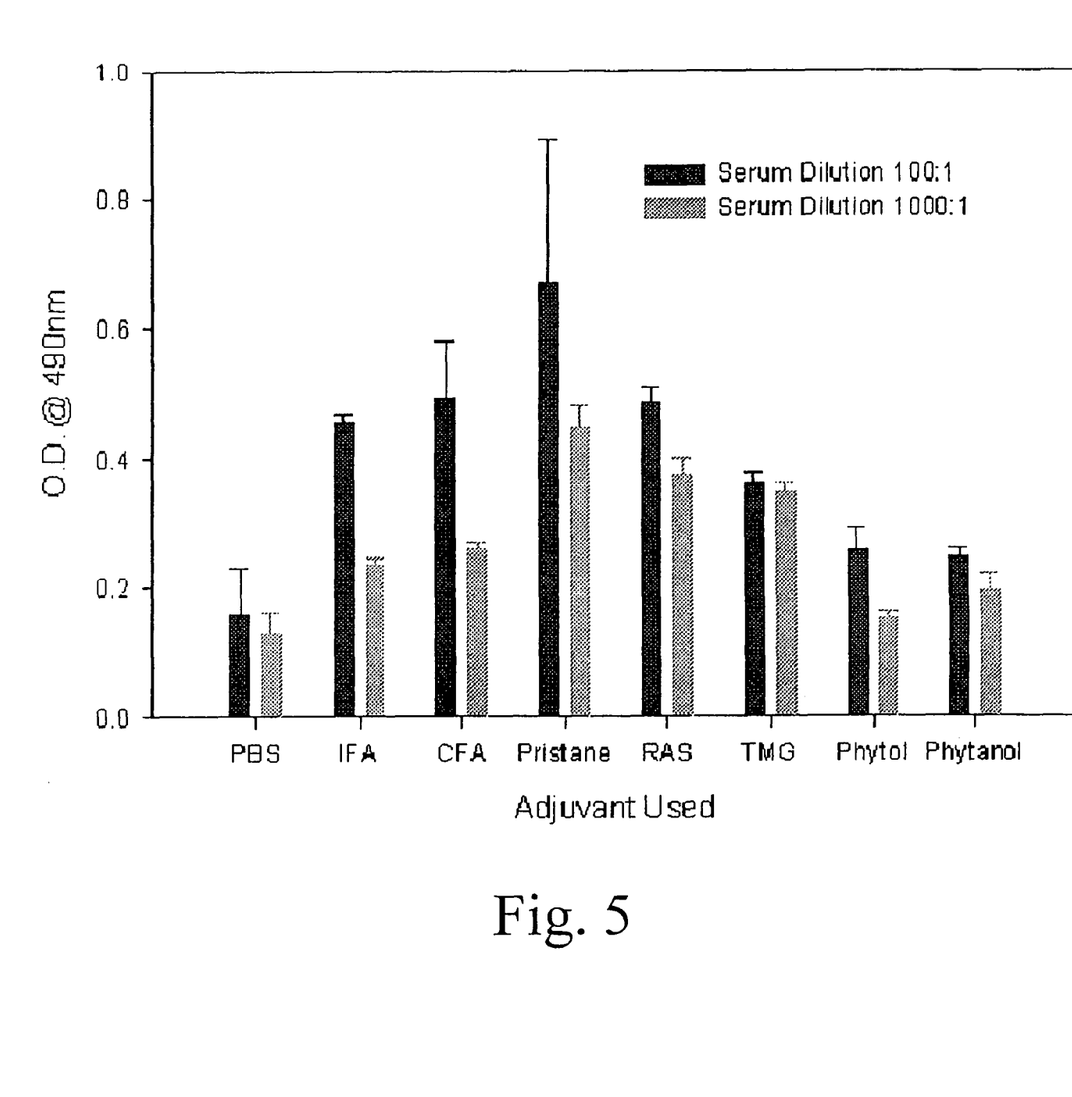
FIG. 5 is a graph illustrating the side effects due to autoimmunity (anti-DNA antibody response) elicited from various adjuvants.

In each set of experiments, groups of 5 mice were primed with an environmental antigen phthalate (Lim and Ghosh, Immunology, 110:482-492, 2003) as a conjugate (mg/ml) with keyhole limpet hemocyanin (KLH) in different adjuvants as shown in FIG. 5. Phytol and phytanol showed statistically insignificant anti-DNA response, whereas all other adjuvants induced significant autoimmune response.

Anti-Hapten Ab Response without Autoreactive Response

Experimental BALB/c mice (n=6) were grouped and primed intraperitoneally with phthalate-KLH conjugates emulsified in each adjuvant. Control groups of mice were immunized with phosphate buffered saline (PBS). Boosters were given at 10-day intervals. The mice were bled through retro-orbital veins five days after each immunization. (reference describing this type of experiments: So-Yon Lim and Swapan K. Ghosh, Immunology, 110:482-492, 2003)

Figure 6:
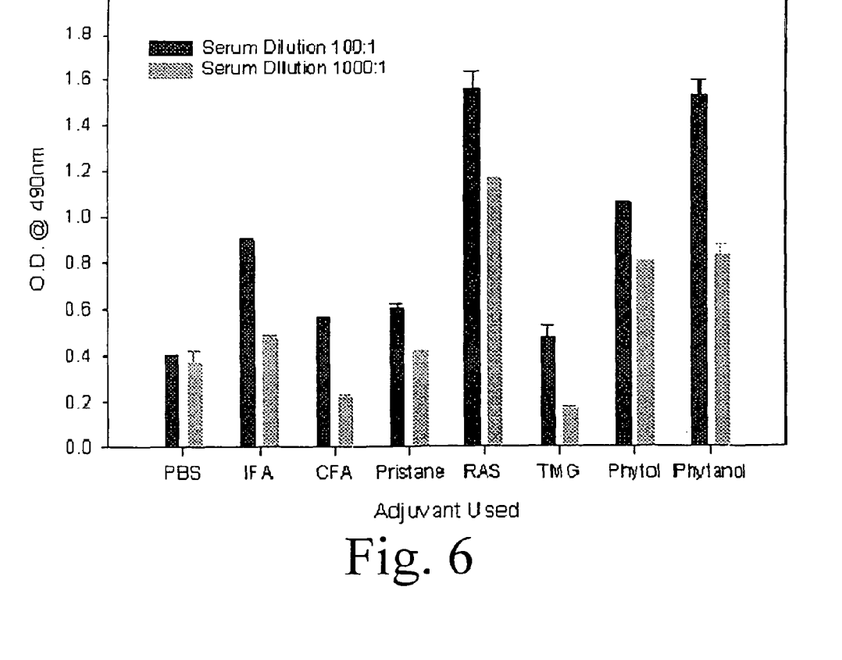
FIG. 6 is a graph comparing various commercially available adjuvants with phytol derivatives for an anti-phthalate antibody response.

ELISA was performed to assess anti-phthalate humoral responses on phthalate-BSA coated plates. The results in FIG. 6. clearly indicate phytanol is better than commonly used CFA/IFA and is as good as commercially available Ribi Adjuvant system (RAS) which is primarily used for humoral antibody response.

Comparison of Antibody Isotype Induced

Figure 7:
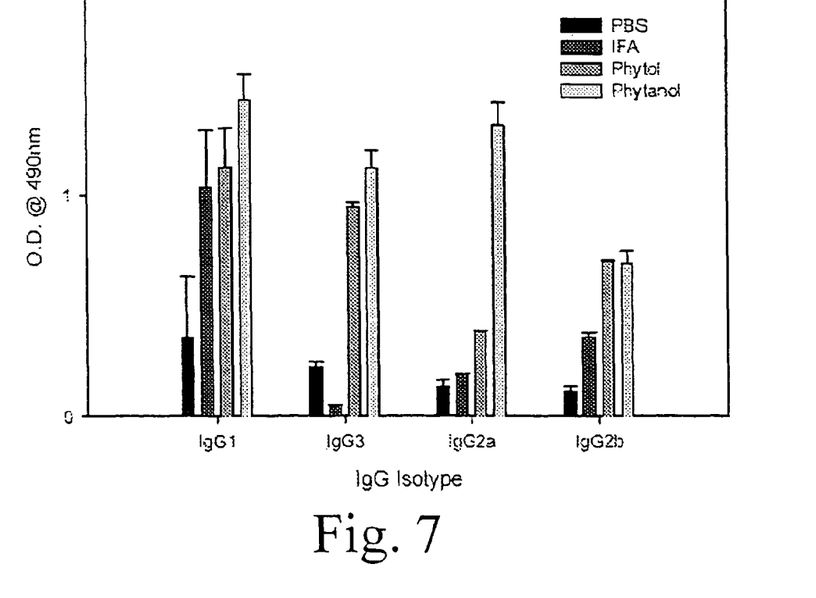
FIG. 7 is a graph illustrating the comparison of the various adjuvants including phytol and phytanol to induce IgG2a antibody isotype response.
Figure 8:
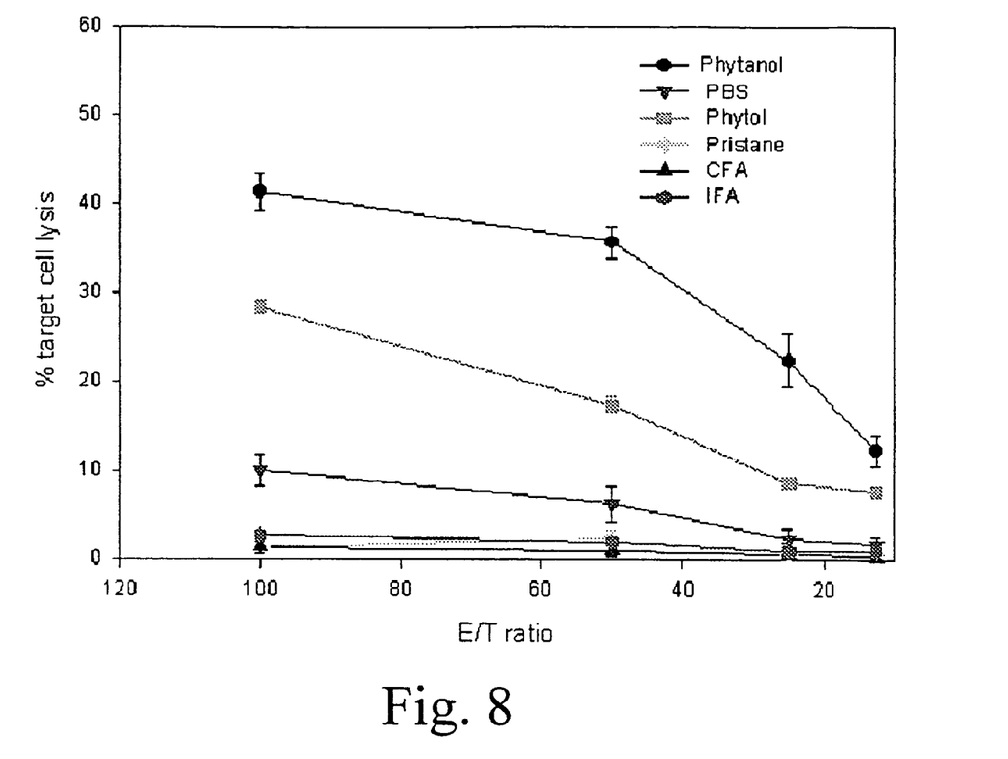
FIG. 8 is a graph illustrating the induction of tumor-specific killer T cells by both phytol and phytanol.

Sera from the above were also analyzed for different antibody isotype using commercially available isotyping kit. Results in FIG. 7 clearly showed the ability of phytol and phytanol to induce IgG2a antibody isotype, which is the most effective in activating complement and antibody-dependent cellular cytotoxic mechanisms. This induction of IgG2a antibody is therapeutically very useful for treatment of viral infection and cancer.

Induction of Tumor-Specific Cytotoxic (Killer) T Cells

A number of mice (BALB/c mice) were divided into four groups of six mice each. Each group was treated with intraperitoneal injections of one of six adjuvant preparations. The adjuvant preparations were selected from IFA, phytol, and phytanol. A control group was injected intraperitoneally with PBS. Five days after the initial injections, each of the mice was injected with a live tumor challenge (5×10⁶ of 2C3 B-cell lymphoma). Splenocytes were obtained form the tumor-challenged mice at the eighth day after the initial injections. The collected splenocytes were stimulated with killed 2C3 cells in vitro for five days. Effector cells were harvested from this preparation after five days of incubation. The effector cells were used in the 51Cr-release cytotoxic T lymphocyte (CTL) assay according to the procedure published in Chakrabarti D. and Ghosh S. K.: Cellular Immunology 144:445-464, 1996; Santra S. and Ghosh S. K.: cancer Immunol. Immunotherpy, 44:291-300, 1997; Laxmanan S., Stuart G. W. and Ghosh S. K. Ghosh, Cancer Immunol. Immunotherapy, 50:437-444, 2001; So-Yon Lim and Swapan K. Ghosh, Immunology, 110: 482-492, 2003.

From the above analysis it can be observed that phytol can be used as an effective component in a wide variety of pharmaceutical formulations and, in particular, shows promise as a highly effective adjuvant for vaccines. The present invention contemplates modifications as would occur to those skilled in the art. It is also contemplated that compositions and formulations embodied in the present invention can be altered or added to other formulations as would occur to those skilled in the art without departing from the spirit of the present invention.

Unless specifically identified to the contrary, all terms used herein are used to include their normal and customary terminology in the relevant fields of endeavor.

All publications, patents, and patent applications cited in this specification are herein incorporated by reference as if each individual publication, patent, or patent application was specifically and individually indicated to be incorporated by reference and set forth in its entirety herein. Further, any theory of operation, proof, or finding stated herein is meant to further enhance understanding of the present invention and is not intended to make the scope of the present invention dependent upon such theory, proof, or finding.

While the invention has been illustrated and described in detail in the drawings and foregoing description, the same is considered to be illustrative and not restrictive in character, it is understood that only the preferred embodiments have been shown and described and that all changes and modifications that come within the spirit of the invention are desired to be protected.

What is claimed is:

1. An immunogenic composition comprising:
   a vaccine antigen;
   an adjuvant component comprising phytol, phytanol, or a phytol derivative wherein the phytol derivative is of the following formula:

wherein $R^1$ is selected from the group of chemical moieties, ions, or radicals consisting of: $Br^-$, $Cl^-$, $I^-$, $-NH_2$, $-NO_2$, $OH$, $PO_4^=$, $HPO_4^-$, $NHR^2$, $OC(O)R^2$, $OR^2$, wherein $R^2$ is a hydrocarbyl having 1 to 10 carbon atoms or a carbohydrate;
   wherein the vaccine antigen is homogenously dispersed in the adjuvant component;
   and optionally a carrier.

2. The composition of claim 1 wherein the adjuvant component comprises phytol.

3. The composition of claim 1 wherein the adjuvant component comprises phytanol.

4. The composition of claim 1 wherein the adjuvant component comprises a phytol derivative selected from the group consisting of: phytanol; 3,7,11,15-tetramethyl-1-hexadecanyl acetate; 1-chloro-3,7,11,15-tetramethyl hexadecane; 1-iodo-3,7,11,15-tetramethyl hexadecane; 1-amino-3,7,11, 15-tetramethyl hexadecane; 1-methyl amino-3,7,11,15-tetramethyl hexadecane; stereoisomers and mixtures thereof.

5. The composition of claim 1 wherein the antigen includes a T-independent antigen.

6. The composition of claim 5 wherein the antigen is selected from the group consisting of polysaccharides, pneumococcus polysaccharides, bacterial lipopolysaccharides, synthetic lipopolysaccharides, and hapten-polysaccharide conjugates.

7. The composition of claim 1 wherein the vaccine antigen comprises a T-dependent antigen.

8. The composition of claim 7 wherein the vaccine antigen is selected from the group consisting of: proteins, peptides, lipoproteins, glycoproteins, gangliosides, cerebrosides, nucleoproteins, eukaryotic cellular isolates, and prokaryotic cellular isolates.

9. The composition of claim 1 wherein the carrier is sterile water at pH 7.0.

10. The composition of claim 1 wherein the carrier comprises physiological buffers that include carbonates, bicarbonates, phosphates.

11. The composition of claim 1 wherein the composition is an oil-in-water emulsion.

12. The composition of claim 11 further comprising a surfactant or emulsifier.

13. The composition of claim 12 wherein the emulsifier is selected from the group consisting of: phospholipids, lysophosphoglycerides, spingomyelin, phosphatidyl choline, phosphatidyl ethanolamine, phosphatidyl inositol and mixtures thereof.

14. The composition of claim 1 wherein the adjuvant component and the vaccine antigen are present at a weight ratio of between about 1:4 to about 1:1.

15. The composition of claim 1 wherein the composition is in a unit dosage form.

16. The composition of claim 1 wherein $R^1$ is $Br^-$, $Cl^-$; $I^-$; $-NH_2$, $-NO_2$, OH, $PO_4^=$, $HPO_4^-$, $NHR^2$, $OC(O)R^2$, $OR^2$, wherein $R^2$ is a hydrocarbyl having 1 to 10 carbon atoms or a carbohydrate.

17. The composition of claim 1 wherein $R^1$ is $Cl^-$.

18. The composition of claim 1 wherein $R^1$ is $I^-$.

19. The composition of claim 1 wherein $R^1$ is $-NH_2$.

20. The composition of claim 1 wherein $R^1$ is $OC(O)R^2$ or $OR^2$, wherein $R^2$ is mannitol.

\* \* \* \* \*